(12) United States Patent
Yang et al.

(10) Patent No.: US 10,758,169 B2
(45) Date of Patent: Sep. 1, 2020

(54) METHOD AND APPARATUS FOR COLLECTING AND ANALYZING URINE SAMPLES

(71) Applicants: Cheng Yang, Shandong (CN); Long Di, Sichuan (CN); Longze Chen, Shanghai (CN); Cao Dong, Shandong (CN)

(72) Inventors: Cheng Yang, Shandong (CN); Long Di, Sichuan (CN); Longze Chen, Shanghai (CN); Cao Dong, Shandong (CN)

( * ) Notice: Subject to any disclaimer, the term of this patent is extended or adjusted under 35 U.S.C. 154(b) by 0 days.

(21) Appl. No.: 16/639,244

(22) PCT Filed: Oct. 30, 2018

(86) PCT No.: PCT/US2018/058259
§ 371 (c)(1),
(2) Date: Feb. 14, 2020

(87) PCT Pub. No.: WO2019/089628
PCT Pub. Date: May 9, 2019

(65) Prior Publication Data
US 2020/0205717 A1 Jul. 2, 2020

Related U.S. Application Data

(60) Provisional application No. 62/578,615, filed on Oct. 30, 2017.

(51) Int. Cl.
*A61B 5/20* (2006.01)
*E03D 11/13* (2006.01)
*A61B 10/00* (2006.01)

(52) U.S. Cl.
CPC .............. *A61B 5/207* (2013.01); *A61B 5/208* (2013.01); *A61B 10/007* (2013.01); *E03D 11/13* (2013.01)

(58) Field of Classification Search
None
See application file for complete search history.

(56) References Cited

U.S. PATENT DOCUMENTS 3,591,290 A 7/1971 Zinner et al.
4,393,881 A * 7/1983 Shah .................... A61B 10/007
600/573

(Continued)

FOREIGN PATENT DOCUMENTS

CN 1118626 A 3/1996
CN 1118627 A 3/1996

(Continued)

*Primary Examiner* — Jill A Warden
*Assistant Examiner* — Brittany I Fisher
(74) *Attorney, Agent, or Firm* — Altman & Martin; Steven K Martin

(57) ABSTRACT

A urine collecting and analyzing apparatus that mounts on a toilet. The apparatus has a housing that mounts to or is integrated into the rim of the toilet bowl and has an opening for access to the bowl. The housing has a collector compartment and a controller compartment. A collector cup fits under the collector compartment extends over the bowl in a retracted position and in a collecting position. When in the collecting position, the cup captures urine released by a user. The cup is connected to a measurement chamber by a transfer tube. The urine moves through the transfer tube from the cup to the measurement chamber to a predetermined threshold volume and level. A controller in the controller compartment reads sensors and transmits sensor data to a device for storage and display.

12 Claims, 12 Drawing Sheets

(56) References Cited

U.S. PATENT DOCUMENTS

| | | | |
|---|---|---|---|
| 4,554,687 A | 11/1985 | Carter et al. | |
| 4,636,474 A | 1/1987 | Ogura et al. | |
| 4,901,736 A * | 2/1990 | Huang | E03D 11/02 |
| | | | 600/573 |
| 4,961,431 A * | 10/1990 | Ikenaga | A61B 5/14507 |
| | | | 600/573 |
| 5,062,304 A | 11/1991 | Van Buskirk et al. | |
| 5,073,500 A | 12/1991 | Saito et al. | |
| 5,111,539 A | 5/1992 | Hiruta et al. | |
| 5,184,359 A | 2/1993 | Tsukamura et al. | |
| 5,625,911 A * | 5/1997 | Nakayama | G01N 33/493 |
| | | | 4/661 |
| 5,720,054 A | 2/1998 | Nakayama et al. | |
| 5,730,149 A | 3/1998 | Nakayama et al. | |
| 5,913,832 A * | 6/1999 | Sagalovich | A61B 10/007 |
| | | | 600/1 |
| 6,212,698 B1 * | 4/2001 | Stingley | A61B 10/007 |
| | | | 4/144.1 |
| 8,091,848 B1 * | 1/2012 | Reed | A61B 10/007 |
| | | | 220/737 |
| 8,690,794 B1 | 4/2014 | Gallardo | |
| 2001/0031500 A1 * | 10/2001 | Kawamura | G01N 21/31 |
| | | | 436/55 |
| 2001/0031913 A1 * | 10/2001 | Ito | A61B 5/14507 |
| | | | 600/300 |
| 2004/0267158 A1 * | 12/2004 | Paasch | A61B 10/007 |
| | | | 600/573 |
| 2015/0359522 A1 | 12/2015 | Recht et al. | |
| 2017/0135622 A1 * | 5/2017 | Shimokawa | A61B 5/208 |
| 2017/0322197 A1 | 11/2017 | Hall et al. | |
| 2018/0055489 A1 * | 3/2018 | Kramer | G01N 33/50 |
| 2018/0184906 A1 * | 7/2018 | Prokopp | A61B 5/207 |
| 2019/0046164 A1 * | 2/2019 | Kramer | A61B 10/007 |
| 2019/0298316 A1 | 10/2019 | Kashyap et al. | |

FOREIGN PATENT DOCUMENTS

| | | |
|---|---|---|
| CN | 101887065 B | 10/2012 |
| CN | 202745164 U | 2/2013 |
| CN | 203042108 U | 7/2013 |
| CN | 103924648 A | 7/2014 |
| CN | 104499547 A | 4/2015 |
| CN | 204435522 U | 7/2015 |
| CN | 104712037 A | 4/2016 |
| CN | 104790487 A | 5/2016 |
| CN | 104790487 B | 5/2016 |
| CN | 104763032 B | 9/2016 |

* cited by examiner

METHOD AND APPARATUS FOR COLLECTING AND ANALYZING URINE SAMPLES

TECHNICAL FIELD

The present invention relates to medical diagnoses, more specifically, to an apparatus and method for automatically collecting a urine sample and performing real-time, long-term, and passive bio-markers and bio-indicators detections in the urine.

BACKGROUND ART

As the age of the world's population continues to grow at an unprecedented rate, increasing focus has been put on the periodic and instant measurement of chronic-disease-related bio-markers and bio-indicators. In addition, with the accelerated pace of life, the public has higher expectations on their health outcomes by real-time and long-term health status monitoring.

Urine is an important bodily fluid that includes vital health information that indicates the health status of an individual, such as disease and nutrition levels. Compared to a blood test, fast and accurate measurements based on the bio-markers and bio-indicators in the urine provide a non-invasive and much easier quantitative health-monitoring approach.

Commonly-used at-home urine test methods include a complex manual urine collection process during which the specimen can be easily contaminated. Due to the time-sensitive nature of the urine test, the lack of control in the manual collection and measurement process introduces large variations. In addition, the complexity limits the user's willingness taking the urine test at home.

DISCLOSURE OF THE INVENTION

The present invention is a urine collecting and analyzing apparatus that mounts on a toilet. The apparatus has a housing that either mounts to or is integrated into the rim of the toilet bowl and has an opening in the center for access to the bowl. The housing has a collector compartment on one side and a controller compartment on the other. A collector cup fits under the collector compartment in a retracted position and extends over the bowl in a collecting position. The cup captures urine released by a user when in the collecting position.

The apparatus includes a mechanism for moving the collector cup between the collecting position and the retracted position. The mechanism can be manual or automatic.

A measurement chamber extends downwardly from the controller compartment. The cup is connected to the measurement chamber by a transfer tube. The urine moves through the transfer tube from the cup to the measurement chamber via gravity to at least a predetermined threshold volume and level. A sensor, typically a flow-rate sensor in the transfer tube, is used to determine whether or not the urine has reached the level threshold. The measurement chamber has an overflow outlet to prevent an excess of urine in the measurement chamber.

Sensors for measuring parameters of the urine extend into the measurement chamber below the threshold level. A controller reads the sensors and transmits sensor data to a device for storage and display. Typically, the device is a mobile device, such as a smart phone, that runs an app for personalized configuration, control, monitoring, and data storage.

The apparatus has a flushing mechanism for flushing urine out of the system. The flushing mechanism includes a flush valve fed by a water supply. The valve outlet supplies a flush tube the extends to an opening in the collector compartment floor above the collector cup when in the retracted position. A gasket seals the cup to the collector compartment floor. The measurement chamber has a drain with a drain plug controlled by the controller to open and close the drain. When measurements are complete, the controller opens the flush valve and the drain plug to flush the system.

Objects of the present invention will become apparent in light of the following drawings and detailed description of the invention.

BRIEF DESCRIPTION OF DRAWINGS

For a fuller understanding of the nature and object of the present invention, reference is made to the accompanying drawings, wherein.

BEST MODES FOR CARRYING OUT THE INVENTION

The present invention is a system for sampling and assaying biological excrement such as urine. The present invention has a physical apparatus and a software component.

Physical Apparatus

The apparatus 50 of the present invention is designed to be mounted to a toilet 2. The phrase "mounted to" is intended to encompass both an apparatus that is integrated into the toilet and an after-market apparatus that is designed to be installed on the toilet.

Figure 1:
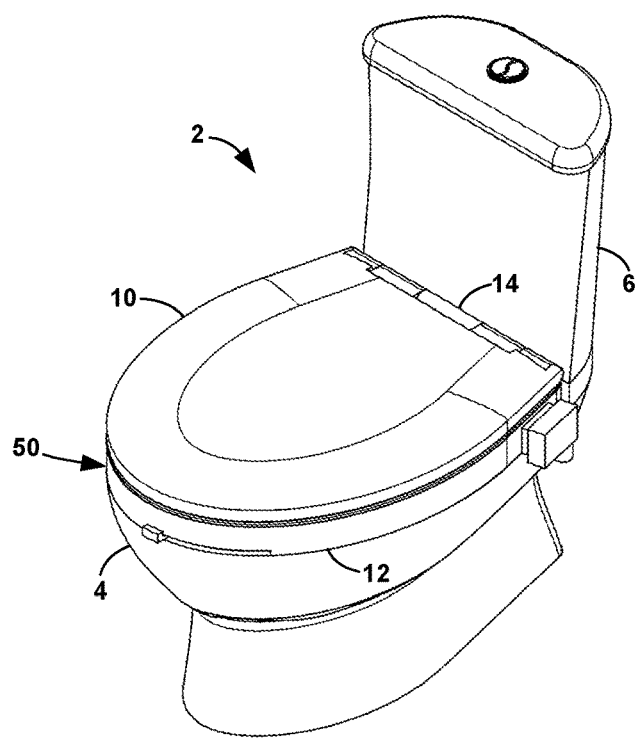
FIG. 1 is a perspective view of the present invention installed on a toilet with the seat and cover closed.
Figure 2:
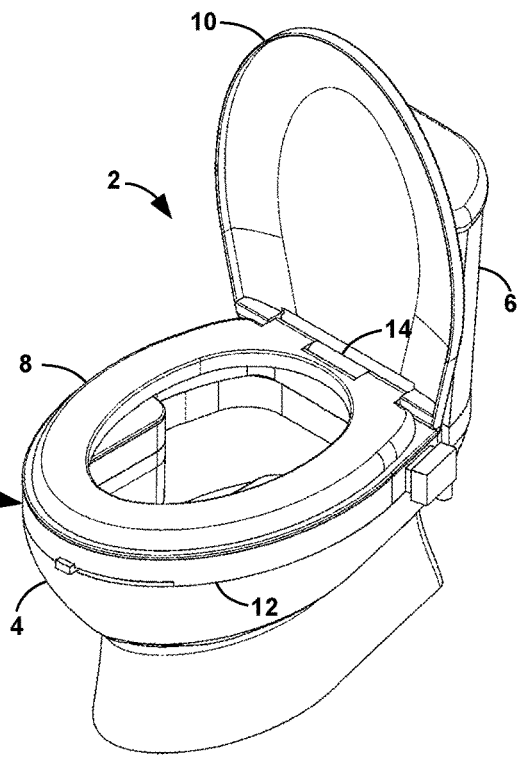
FIG. 2 is a perspective view of the present invention installed on a toilet with the seat closed and the cover open.

The present invention is for conventional or smart toilets 2 that include standard elements: a bowl 4 with a rim 12, a tank 6, and a seat 8. Toilets 2 have bowls 4 that are round or oval, as in FIGS. 1-3. The apparatus 50 can be adapted for either shape. The toilet 2 can have a cover 10, but it is not necessary for operation of the present invention.

The physical apparatus 50 includes five major components: the housing 52, the urine collector 54, the measurement chamber 56, the flush unit 58, and the control unit 60 for data processing and transmission.

Housing 52

Figure 3:
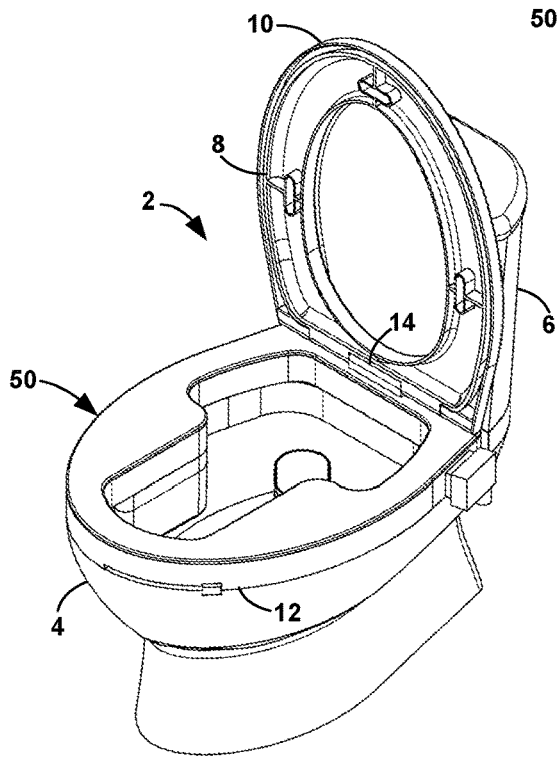
FIG. 3 is a perspective view of the present invention installed on a toilet with the seat and cover open.

The housing 52 sits on the rim 12 of the toilet bowl 4, following the perimeter of the rim 12, as seen in FIG. 3. The housing 52 extends inwardly over the bowl 4 and has an opening 68 in the center for access to the bowl 4. Details of the housing 52 are described below with reference to the other components of the apparatus 50.

The housing 52 is installed on the bowl 4 so that it does not move relative to the bowl 4. The housing 52 can be attached to the bowl 4 using, for example, retaining clips the hook under the rim 12 and the attachment points 14 on the bowl 4 for the seat 8. Because the housing 52 sits atop the rim 12, the seat attachment points 14 of the bowl 4 are not accessible. Consequently, the housing 52 is provided with seat attachment points 70 appropriate for the seat 8.

Alternatively, the bowl 4 is designed with the housing 52 as an integral element.

The housing 52 has a collector compartment 72 extending over the bowl 4 from one side of the housing 52, and a controller compartment 74 extending over the bowl 4 from the other side of the housing 52. The compartments 72, 74 provide space for several other components of the apparatus.

Preferably, the housing 52 is designed to fully hide beneath the toilet seat 8 so that interference with routine toilet use is minimized. Optionally, the housing 52 is that same or similarly to the toilet seat 8.

The housing 52 is composed of one or more rigid materials. Example materials include plastics, ceramics, and metals. Possible plastics include, but are not limited to, urea-formaldehyde (UF), polyvinyl chloride (PVC), and acrylic.

Collector 54

Figure 6:
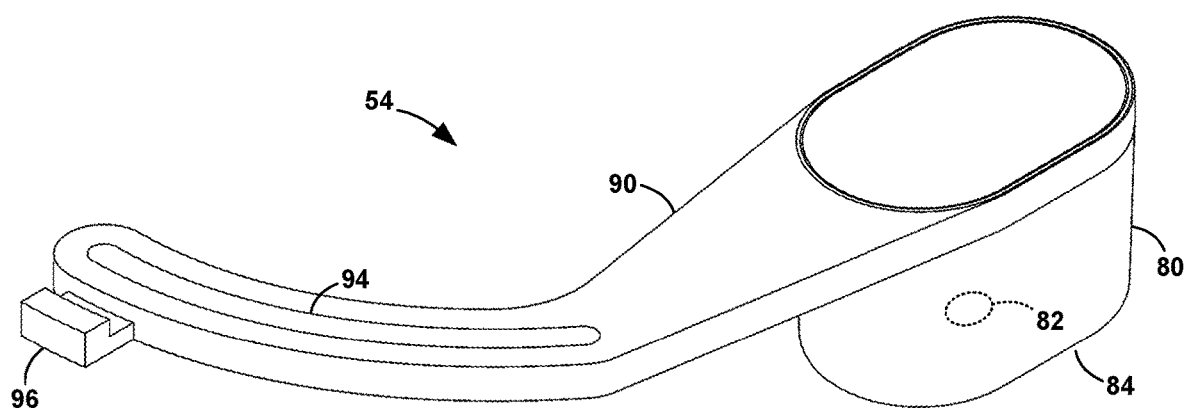
FIG. 6 is a perspective view of the collector.
Figure 7:
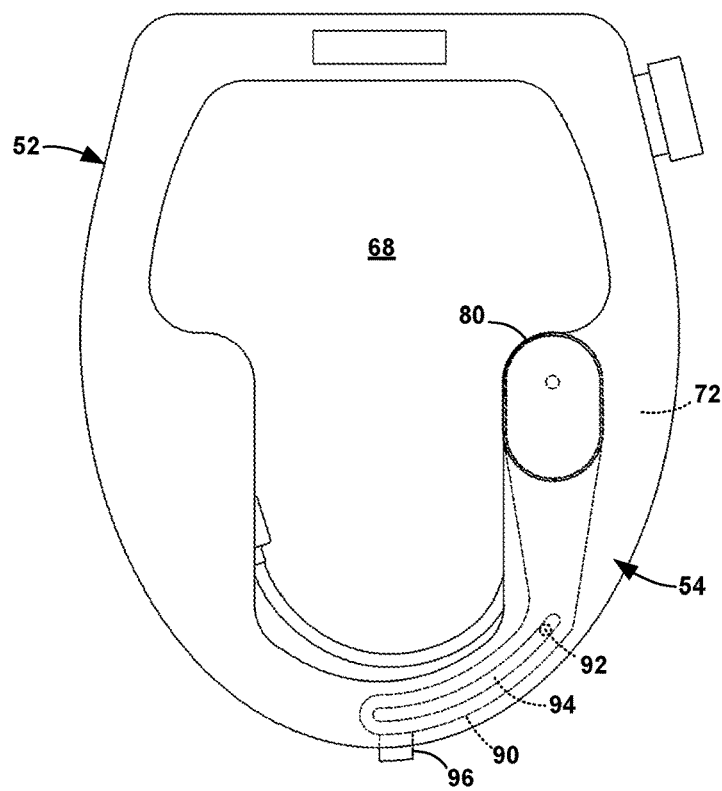
FIG. 7 is a top, partially phantom view of the collector in the retracted position.

The collector 54 collects the urine being released by the user. As shown in FIG. 6, the collector 54 is a collector cup 80. Optionally, the cup 80 includes a porous cover as a splash guard. When not collecting urine, the cup 80 is in its retracted position under the collector compartment 72, as seen in FIG. 7.

Figure 8:
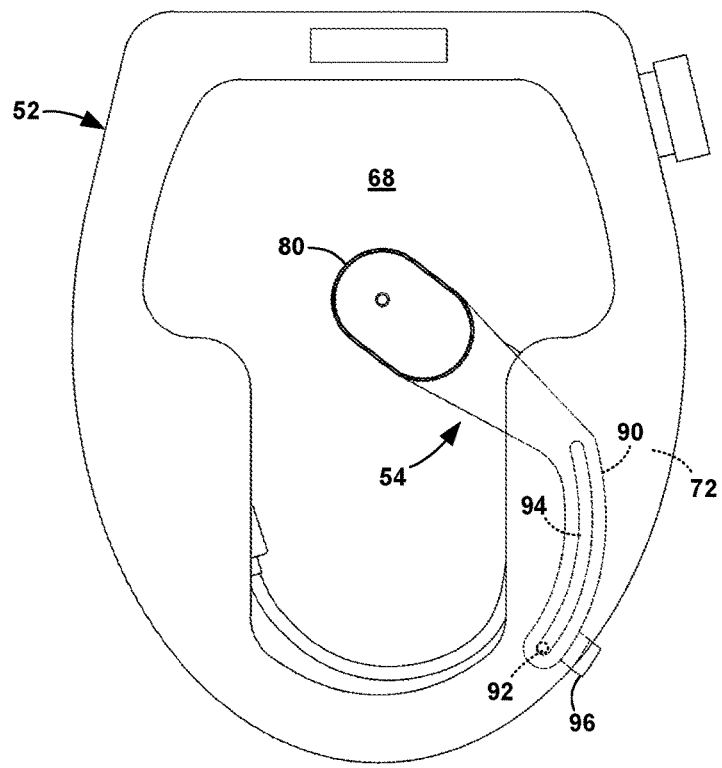
FIG. 8 is a top, partially phantom view of the collector in the collecting position.

A mechanism 88 provides a means for pivoting the cup 80 over the bowl 4 to the collecting position, seen in FIG. 8, for capturing the urine released by the user. In the present design, a curved arm 90 that extends from the cup 80 under the housing 52, following the curve of the housing 52, to the front of the housing 52. A pin 92 extending downwardly from the housing 52 fits in an elongated curved slot 94 in the arm 90. A tab 96 extends approximately 90° from the end of the arm 90 through a slit 98 in the front 76 of the housing 52. As the user pushes the tab 96 in the slit 98 around the perimeter of the housing, the curve of the arm 90 causes the cup 80 to move into the center of the bowl 4. The cup 80 is retracted back under the housing 52 by pushing the tab 96 back to the front 76 of the housing 52. The present invention contemplates that the above-described mechanism can be located at other positions around the housing 52, for example, with the tab 96 at the back of the housing 52 near the toilet tank 6.

The present invention contemplates that any other mechanism that can pivot the cup 80 can be incorporated, including other manual mechanisms, such as a motorized mechanism controlled by a button on the housing 52 or toilet 2 or by a button on the mobile app. An automated mechanism can be programmed to adapt to different users' habits controlled by the control unit 60. For example, the settings for the mechanism can link to the user's ID (described below). The user is required to input the initial settings, e.g. test time, frequency, etc., and when the user approaches the toilet, the mechanism operates as needed.

Figure 9:
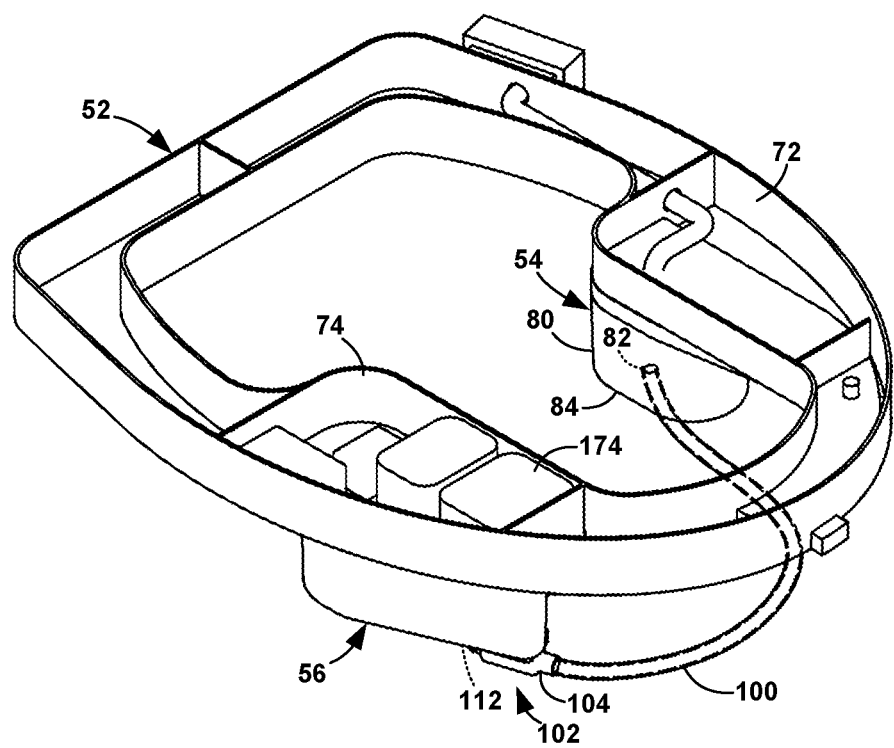
FIG. 9 is a perspective, partial phantom view of the collector and measurement chamber connected by the transfer tube.

A transfer tube 100 attached to an outlet hole 82 at the bottom 84 of the cup 80 connects the cup 80 to the measurement chamber 56, as seen in FIG. 9. Gravity causes urine collected in the cup 80 to flow through the transfer tube 100 from the cup 80 to the measurement chamber 56.

Alternatively, an electric pump (not shown) can be employed to move urine from the cup 80 to the chamber 56. The pump can be designed to be turned on and off by the controller 174 or to turn on when it senses liquid at its inlet port and turned off by the controller 174.

The collector 54 is composed of one or more rigid materials. Example materials include plastics, ceramics, and metals. Possible plastics include, but are not limited to, urea-formaldehyde (UF), polyvinyl chloride (PVC), and acrylic.

Measurement Chamber 56

Figure 4:
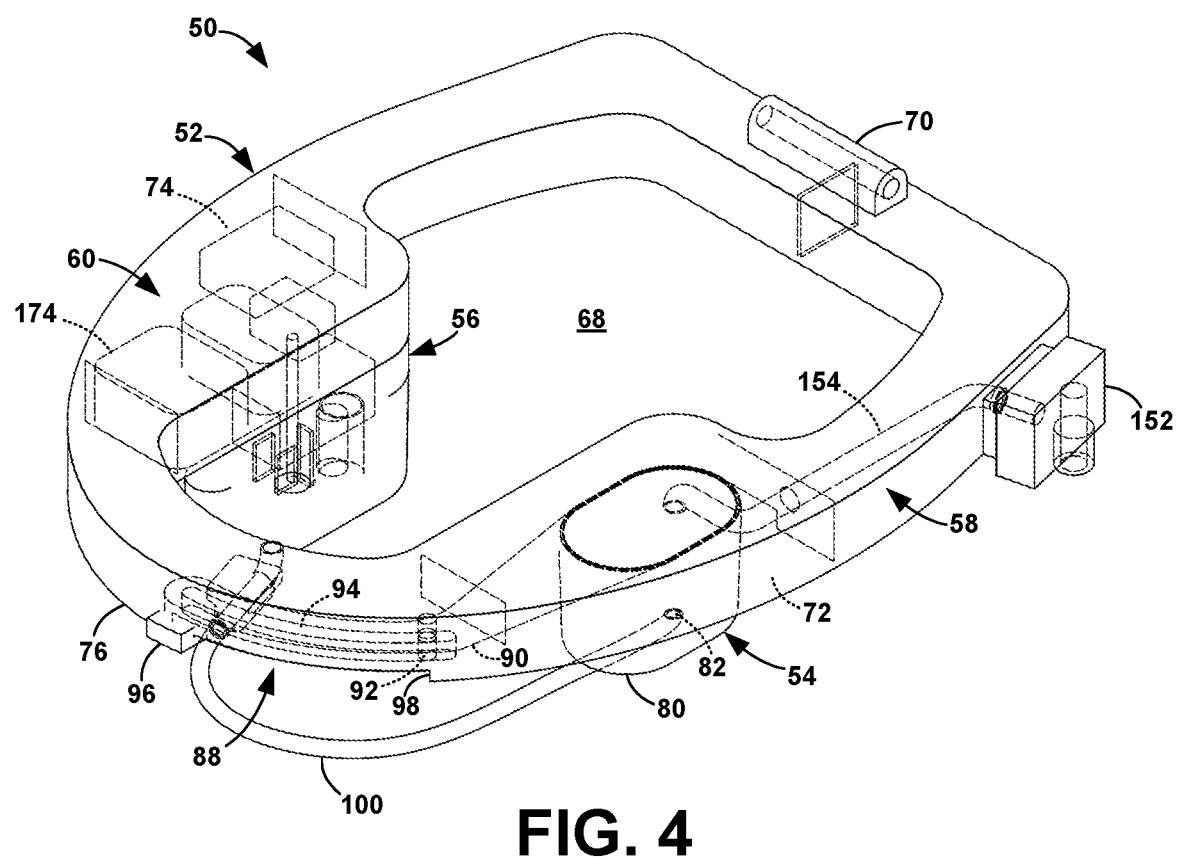
FIG. 4 is a perspective, partially phantom view of several components of the apparatus of the present invention.
Figure 5:
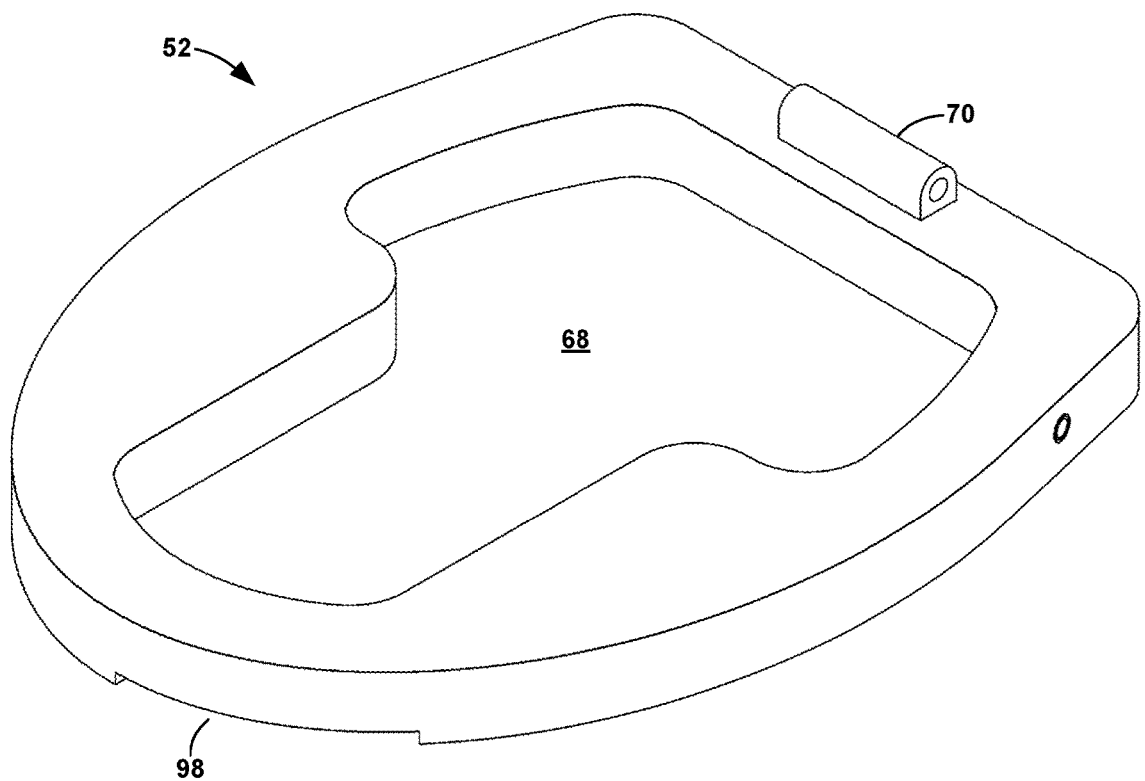
FIG. 5 is a perspective view of the housing.

As shown in FIGS. 4 and 9, the measurement chamber 56 is affixed to the housing 52 below the controller compartment 74. The chamber 56 is fed by the transfer tube 100 from the collector cup 80. The end of the transfer tube 100 is attached to an inlet 112 in the floor 110 of the measurement chamber 56.

Figure 10:
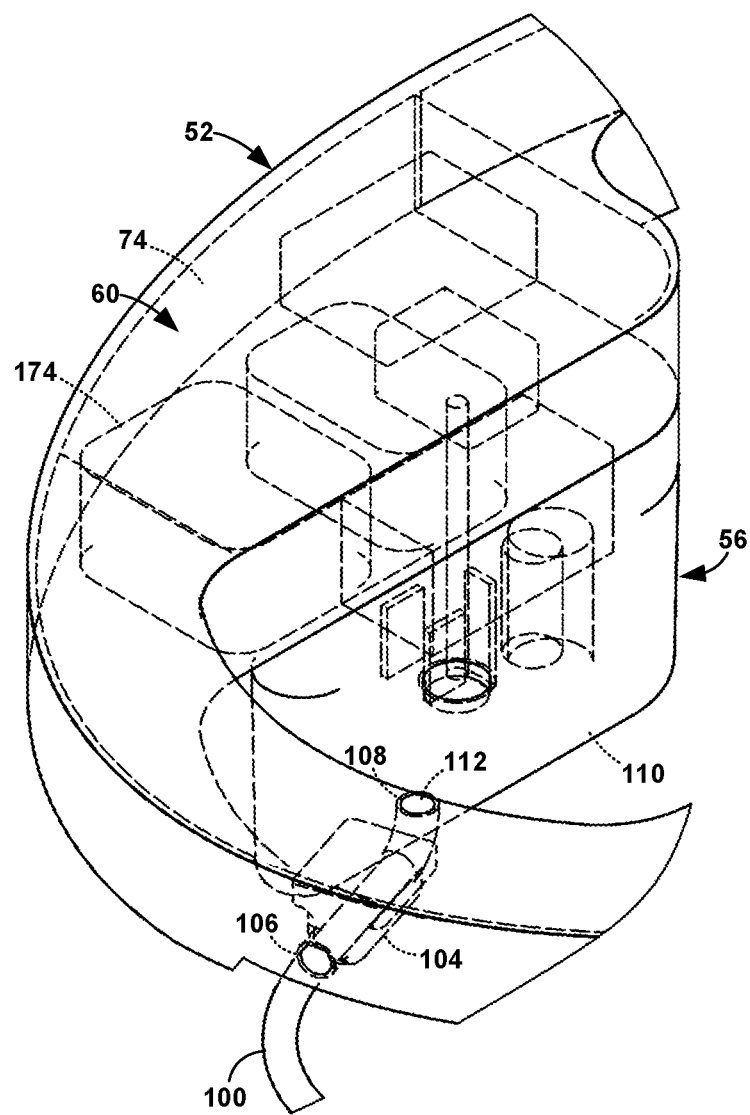
FIG. 10 is a detailed view of the measurement chamber in the housing.

The measurement chamber 56 includes a urine level sensor 102 for determining the urine level in the chamber 56. One mechanism includes a flow-rate sensor 104 that measures the urine flow time and rate so that the volume and level of the incoming urine can be calculated. As shown in FIG. 10, rather than attaching directly to the chamber inlet 112, the end of the transfer tube 100 is attached to the inlet 106 of the flow-rate sensor 104. The outlet 108 of the flow-rate sensor 104 feeds the chamber inlet 112.

Another mechanism for determining urine level employs a mechanical float sensor in the chamber 56 that rises and falls as the urine level changes.

Another mechanism for determining urine level employs an optical sensor that measures the level of urine in the chamber 56. Alternatively, the optical sensor merely tracks a predetermined level and triggers with that level is reached.

Figure 11:
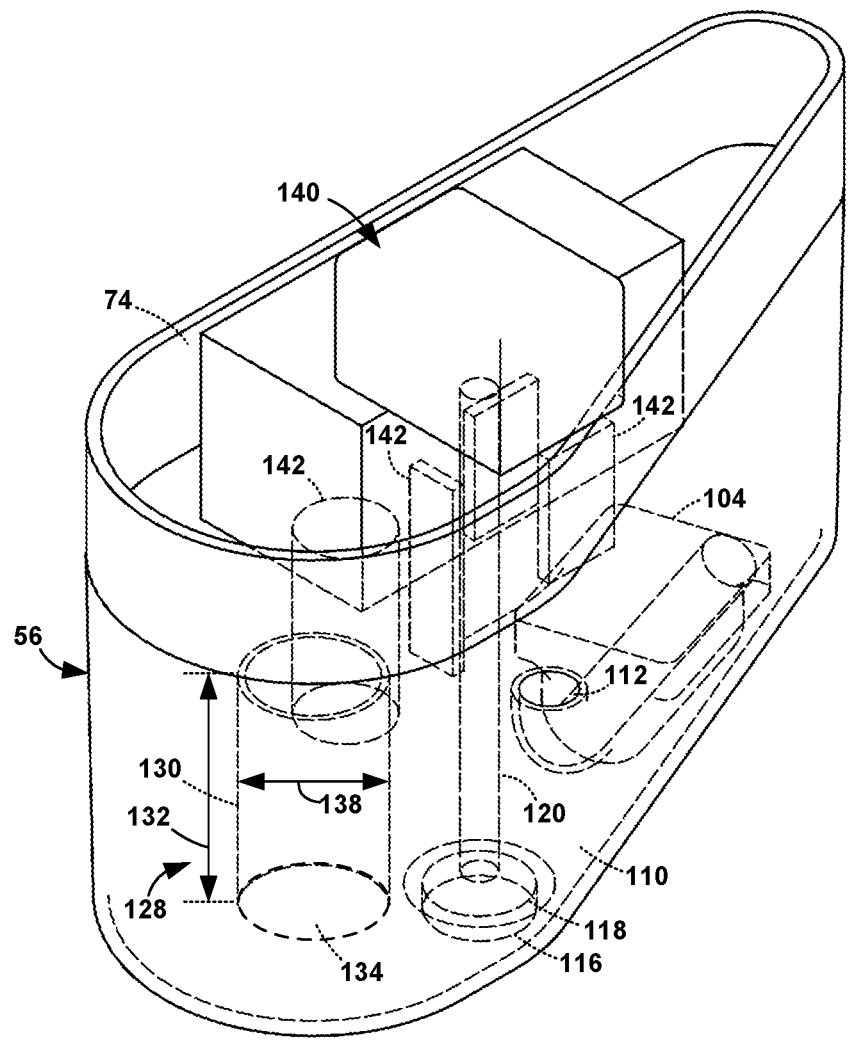
FIG. 11 is a perspective, phantom reverse, view of the measurement chamber.

As shown in FIG. 11, the chamber 56 has an drain 116 in the floor 110 for draining the chamber 56 when testing is complete. A plug 118 opens and closes the drain 116 by means of a solenoid 120. The solenoid 120 is mounted above the chamber 56 in the controller compartment 74 and extends downwardly to the plug 118.

The chamber 56 is designed to ensure that urine can reach and sustain a threshold volume and level required for accurate measurement. The threshold urine volume and level are those at which all of the sensors are immersed in urine to the point that they can sense accurately. The level and volume are dependent on the shape of the chamber 56. In the present design of the chamber 56, for the sensors 142 that are currently employed, the minimum level from the chamber floor 110 is 12 cm and the minimum volume is 10 ml. The present invention contemplates that these values may change depending on the sensors that are employed and that the chamber 56 can be designed with different dimensions.

The chamber 56 has an overflow outlet 128 for maintaining the desired urine level inside the chamber 56 by discharging excess urine from the chamber 56. The overflow outlet 128 is a hollow, cylindrical tower 130 rising from the chamber floor 110. The opening 132 in the top of the tower 130 is lower than the bottom 84 of the cup 80 so that the urine will flow due to gravity to fill the measurement chamber 56 without backing up into the transfer tube 100 and cup 80. Any urine entering the opening 132 in the top of the tower 130 drains through the tower 130, through an opening 134 in the floor 110, and into the bowl 4. The height 136 of the tower 130 from the floor 110 determines the maximum level of the urine in the chamber 56. The tower inside diameter 138 is large enough to discharge urine at least as fast is it comes into the chamber 56 so that the urine level cannot exceed the desired maximum level.

A sensor module 140 resides either in the chamber 56 or above the chamber 56 in the controller compartment 74. Sensors 142 extends downwardly into the chamber 56 below the minimum urine level for accurate measurements. The various sensors can include, but are not limited to, electrochemical sensors, temperature sensors, pH sensors, and chromogenic sensors to test for pregnancy, ovulation, or proteins for urinary tract infections.

The measurement chamber 56 is composed of one or more rigid materials. Example materials include plastics, ceramics, and metals. Possible plastics include, but are not limited to, urea-formaldehyde (UF), polyvinyl chloride (PVC), and acrylic.

Flush Unit 58

The flush unit 58 rinses the system of urine in preparation for the next measurement. The flush unit 58 includes a supply tube 150, a flush valve 152, and a flush tube 154. The flush valve 152 is mounted to the housing 52 so as to not interfere with normal usage of the toilet 2. Typically, it is mounted on the side rear of the housing 52, as in FIGS. 1-4 and 12. The supply tube 150 brings water from a source to the inlet 156 of the flush valve 152. The water source can be the household water supply to the toilet 2 or the toilet tank 6. When sourced from the tank 6, a pump would most likely be needed.

Figure 12:
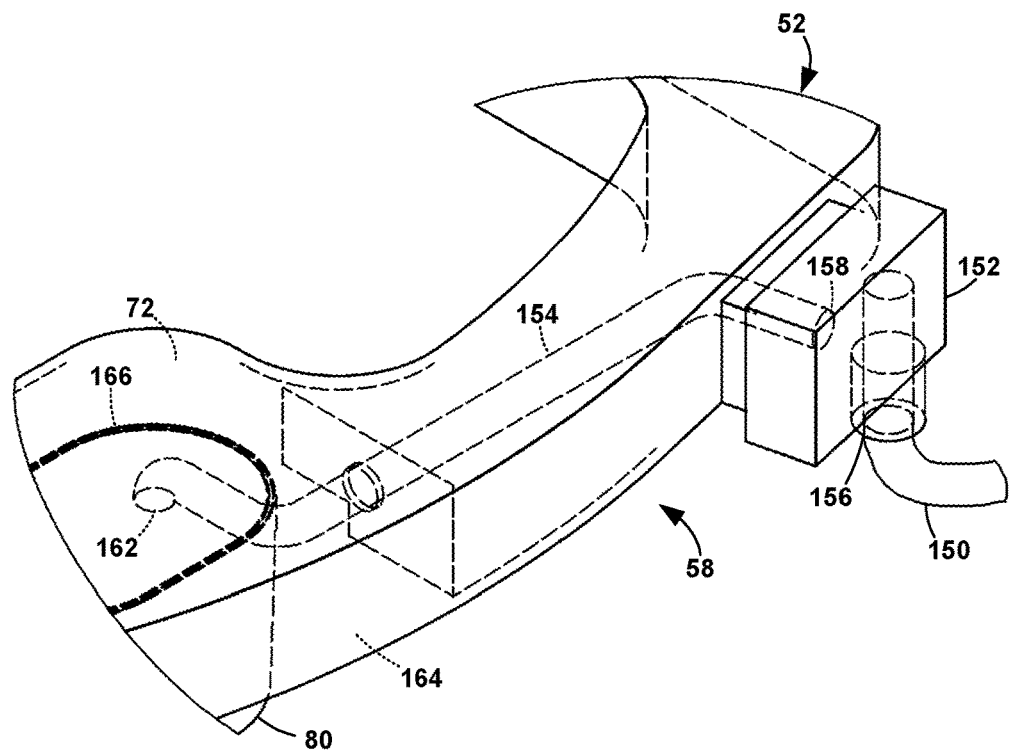
FIG. 12 is a perspective, phantom view of the flush valve and tube.

As shown in FIG. 12, the flush tube 154 extends from the outlet 158 of the flush valve 152, through the housing 52 into the collector compartment 72. The other end of the flush tube is attached to an aperture 162 in the floor 164 of the collector compartment 72 above the cup 80 when the cup 80 is in the retracted position.

The collector cup 80 optionally has an O-ring or other gasket 166 at the top to seal against the floor 164 of the collector compartment 72. The gasket 166 helps to minimize the amount of water that may splash out of the collector 54 during flushing.

Optionally, the flush unit 58 includes coatings in the collector cup 80, transfer tube 100, and measurement chamber 56. The coatings can include non-stick coatings and anti-bacterial coatings. A contemplated coating is a thin-film hydrophobic polymer to provide anti-bacterial and anti-fouling performance, reducing maintenance requirements.

Control Unit 60

Figure 13:
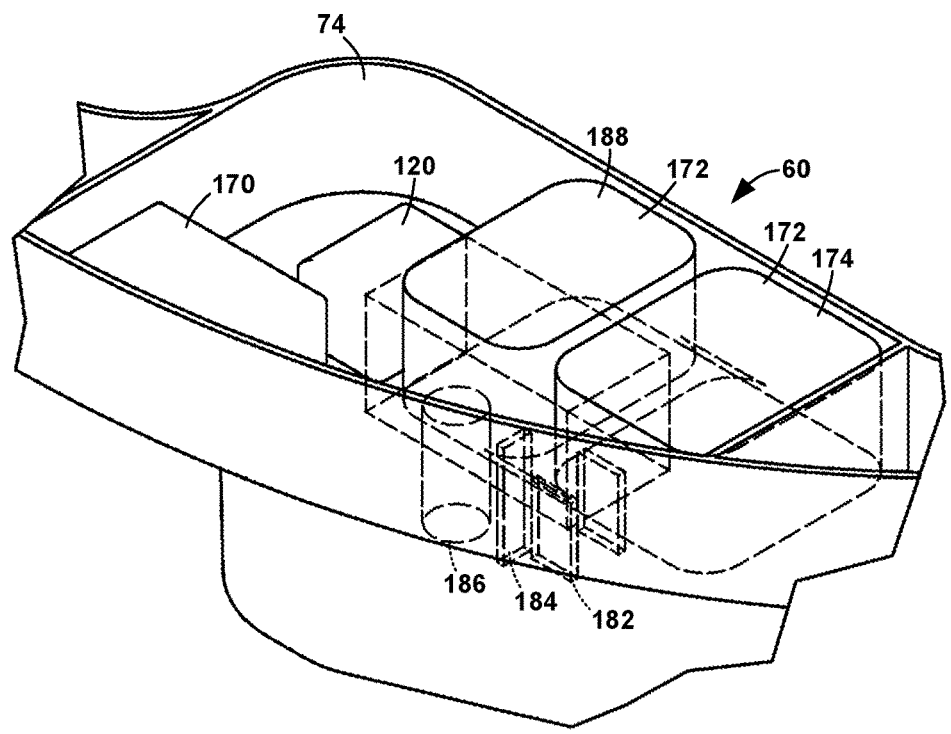
FIG. 13 is a perspective, partial phantom view of the controller compartment.

As shown in FIG. 13, the control unit 60 is located inside the controller compartment 74. The control unit 60 has a power supply 170 and a control module 172. The control module 172 has several functions, including control of the hardware, data processing, and data communications, as described below.

The power supply 170 powers the system. The power source can be batteries or AC power. Batteries are mounted in a battery pack within the housing 52. The battery pack can be accessed via a cover on the housing 52 or the battery pack can be installed by sliding it into the side of the housing 52. The AC power can be via the smart toilet the system is attached to or integrated into or directly by an AC wall plug. The power supply 170 provides all the necessary voltages required by the system components.

System Functional Architecture

Figure 14:
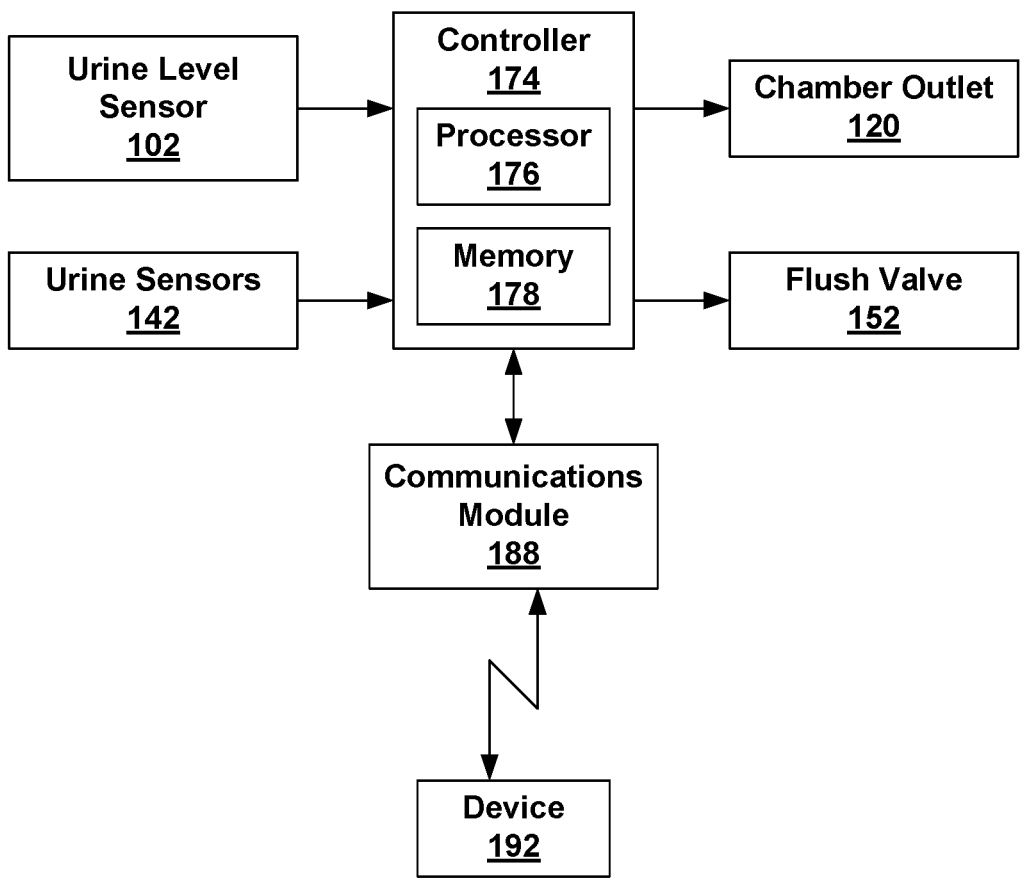
FIG. 14 is a block diagram of the apparatus.

A block diagram of the hardware of the present invention is shown in FIG. 14. The control module 172 includes a controller 174 with a processor 176, memory storage 178, and input/output signals. The controller 174 may have one or more processors. For example, in a two-processor controller 174, one processor provides system control and the other processor processes data.

Components providing inputs to the controller 174 include the urine level sensor 102, a potentiost at 182, a temperature sensor 184, a pH sensor 186, and, optionally, a button panel to identify the current user, as described below. Output signals include control for the chamber outlet solenoid 120 and the flush valve 152. The control module 172 includes a communication module 188 that communicates with a user interface device 192, such as a mobile phone, via Bluetooth, WiFi, NFC, and/or other wireless communication protocols.

Figure 15:
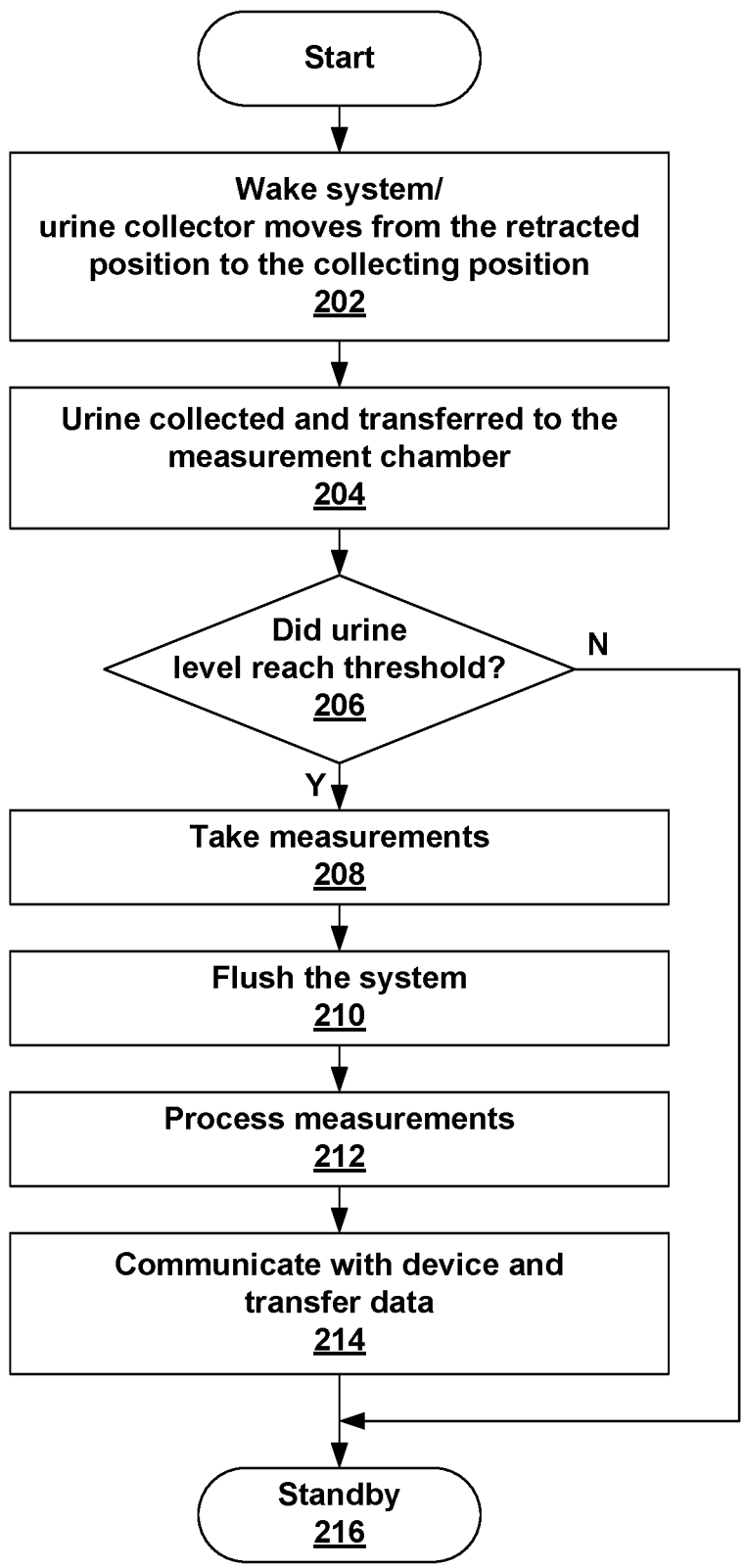
FIG. 15 is a flow diagram of the collection and measurement process.
Figure 16:
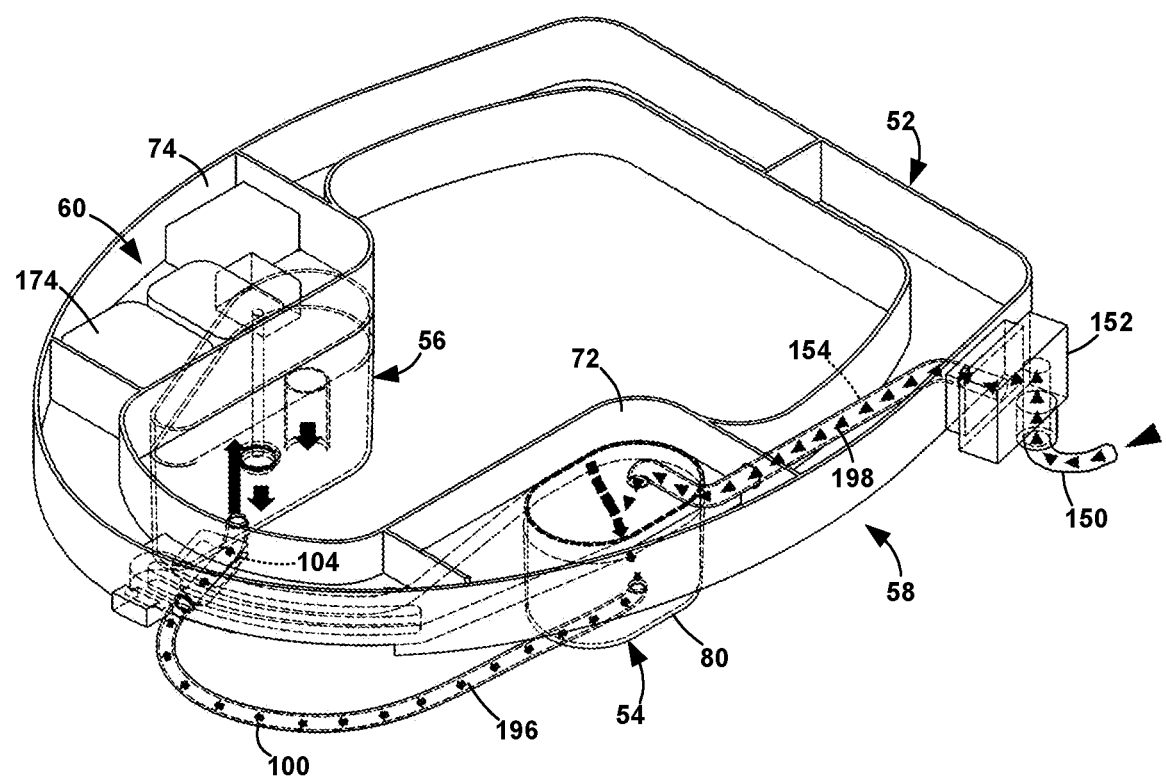
FIG. 16 is a schematic diagram of urine and water flow.

A flow diagram of the collection and measurement process is shown in FIG. 15 and a schematic diagram of liquid flow is shown in FIG. 16.

Optionally, the system can be designed for multiple users. As such, the system needs a way to identify the current user. Three methods are described below, but the present invention contemplates that any method of the identifying the current user can be implemented.

In the first method of identifying the current user, the system includes a panel of buttons, one for each user. Prior to the urine test, the user presses the appropriate button to inform the system who is being tested.

In the second method, the communication module 188 is always on and constantly monitoring Bluetooth signals. When the system detects the Bluetooth signal from a user's mobile device, the system uses the strength of the Bluetooth signal to determine whether or not the user is using the system.

In the third method, the system is integrated into a home health/monitor system that can detect where a person is and who he/she is. The system uses this information to determine who the current user is.

To reduce the energy cost and extend the useful life of the device, the system remains in a low-power standby state when not in use. The system is awaken by one or more of several different contemplated triggers, as at 202. One trigger can be the act of manually moving the cup 80 from the retracted position to the collecting position. The controller 174 uses a switch or position sensor to recognize when the cup 80 is in the collecting position. Another trigger can occur when a flow-rate sensor 104 detects urine flow into the measurement chamber 56. Another trigger can be a manual pushbutton, for example, a button on a user selection panel described above, that is sensed by the controller 174.

Urine collected in the cup 80 flows into the measurement chamber 56 via the transfer tube 100, as at 204 in FIGS. 15 and 196 in FIG. 16. The urine level sensor determines whether or not to start the measurements. More specifically, the controller 174 triggers the sensors 142 to measure the urine if the urine level reaches a predetermined threshold value in a predetermined amount of time, as at 206.

The controller 174 takes the time it needs to read the measurement sensors 142, as at 208.

When all the desired measurement data is acquired or if the urine volume does not reach the threshold within the amount of time or, the controller 174 performs the flush procedure, as at 210. If the cup 80 is automatically controlled, the cup 80 is pivoted to the retracted position. If the cup 80 is manually controlled, the user is reminded to retract the cup 80 by some type of indicator. The indicator can be a visual, such as a lamp lighting, or aural, such as a tone sounding. The indicator can be via the communication module 188 sending a reminder to the device 192.

When the controller 174 senses that the cup 80 is in the retracted position, the controller 174 triggers the solenoid 120 to lift the plug 122 to open the chamber drain 116, allowing the chamber 56 to drain. The controller 174 opens the flush valve 152, thereby allowing water to flow through the flush tube 154 into the cup 80, as at 198. Optionally, the controller 174 can wait to open the flush valve until it senses that the user has flushed the toilet. This sensor can be a switch on the flush handle, a water level sensor in the tank 4, or any other mechanism for sensing that the toilet 2 has been flushed.

The water follows the path of the urine 196, through the transfer tube 100 and into the measurement chamber 56, where the water flushes out the urine through the chamber drain 116 and overflow outlet 128.

After a predetermined amount of time, typically 5 to 15 seconds, the controller 174 closes the flush valve 152. A predetermined amount of time later, typically 10-20 seconds, the controller 174 instructs the solenoid 120 to close the chamber drain 116. The extra time allows the chamber 56 to fully drain.

Prior to, during, and/or after the flush procedure, the controller 174 performs its processing on the sensor data, described below, as at 212. After processing is complete, the controller 174 communicates the data to the device 192, described below, as at 214. Optionally, once the collection, measurement, and communication process is complete, the system, with the exception of the initial trigger sensing, is put into a standby mode to save energy, as at 216.

Data Processing

The controller 174 reads data from the sensors 142. In the current design that sensors 142 are a potentiostat 182, a temperature sensor 184, and a pH sensor 186. The potentiostat 184 is a three-terminal analog feedback control circuit that measures electric current exchange between electrodes and chemicals in the urine. The voltages with regard to the reference and currents at which the exchange happen can be measured, and the corresponding information is sent to the controller for processing.

Data from the sensors 142 is processed. Optionally, several digital filters are used to smooth the process. A five-point moving-average filter is applied in the data parsing algorithm to smooth an array of sampled data and eliminate high frequency noise. The concept of moving average is simple and it is based on a low-pass finite impulse response (FIR) filter. The filter takes multiple samples of sensor data for every iteration, calculates the average of the samples and produces a single output.

Besides the moving-average filter, other low-pass filters can be employed to avoid the aliasing effect during data sampling from the measurement. For example, a fourth-order Butterworth low-pass filter with a cutoff frequency at 100 Hz can be employed to reduce aliasing.

Because aggressive attenuation during the transition band is not required for this application and the Butterworth filter has no ripples at both pass-band and stop-band, it is able to effectively attenuate any signal whose frequency is higher than 200 Hz. In the future, when the sampling frequency goes up, the anti-aliasing filter can be easily redesigned and implemented in the processing loop.

In addition, a peak-finding algorithm can be implemented in the processing loop to identify the peak measurement for the incoming data set, which is crucial for the electrochemistry sensors.

After each test, results are stored as an entry in the on-board persistent storage memory 178. Each entry contains the user ID, the device ID, the time of the test, the raw data, and the processed data. In addition, the entry includes any stored error codes and messages if the test encountered any problems. Preferably, the storage memory 178 is large enough to hold several weeks of data for a single user or 2) at least one week of data for multiple users. If the storage memory 178 runs out of space, a new entry will overwrite the oldest entry of the same user.

After the data is stored, the controller 174 activates the communication module 188, which then waits for the mobile application to connect and synchronize data. After a successful data synchronization, the controller 174 optionally deletes old entries to free up storage.

Mobile App

The mobile app runs on a user device 192, such as a mobile phone or tablet computer. The app connects to the communication module 188 via Bluetooth, WiFi, NFC, or other wireless communication protocol. The app checks for and performs a secure data fetch periodically when connected. Alternatively, the user can manually instruct the app to perform a data fetch, typically after a test.

All of the urine test data can be stored in the app. In addition, the user can store the data with a cloud storage provider as additional storage and/or as backup. The user has the option of deleting all of the test data.

The app presents the test data to the user on the display of the user device 192. FIGS. 17-21 show five major views of the app.

Figure 17:
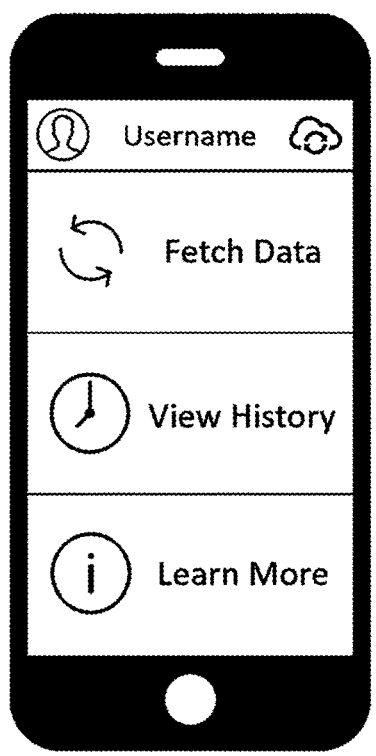
FIG. 17 is an illustration of the mobile app home display.

The dashboard page, shown in FIG. 17, provides the user with several options: 1) fetch new test results from the controller 174 and view them in detail, 2) view the test history, and 3) learn more about urinalysis and related diseases.

Figure 18:
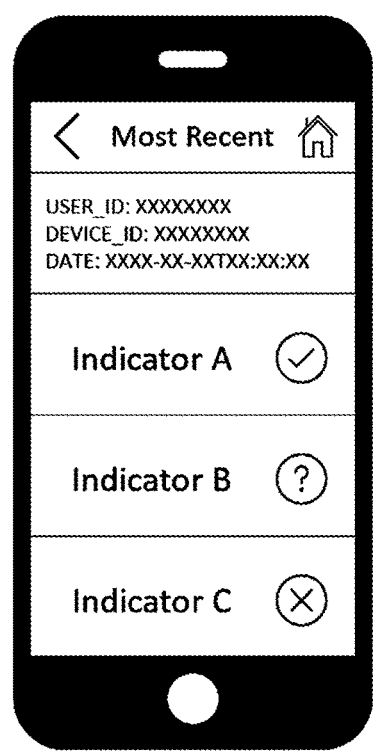
FIG. 18 is an illustration of a mobile app detailed result display.

The detailed result page, shown in FIG. 18, provides a list of the urine indicators that are tested. The results are indicated by different background colors. Specifically, green indicates that it is within normal range, yellow warns the user that there may be a potential risk/issue, and red indicates that the data is invalid and informs the user to perform the test again later.

Figure 19:
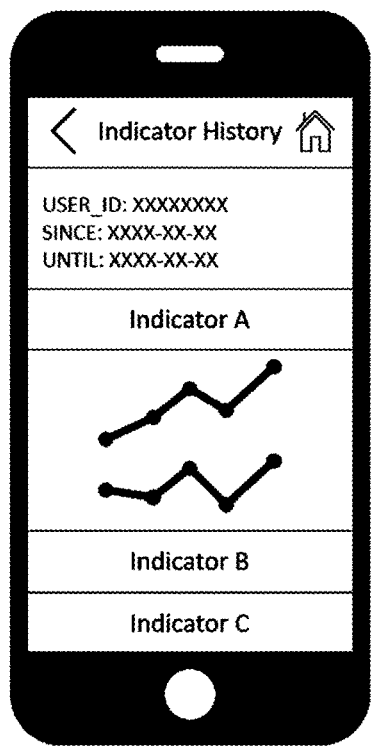
FIG. 19 is an illustration of a mobile app history display.
Figure 20:
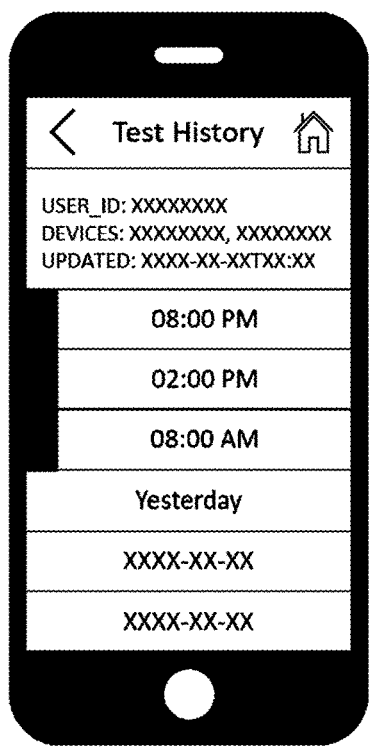
FIG. 20 is an illustration of another mobile app history display.

The indicator history page, shown in FIG. 19, provides the user with a history chart for each indicator. Data collected in the past days or weeks is stored and trackable. Specifically, the test history page, shown in FIG. 20, provides a list of all the tests sorted by data and time. The user can click on each one to view it in the detail page.

Figure 21:
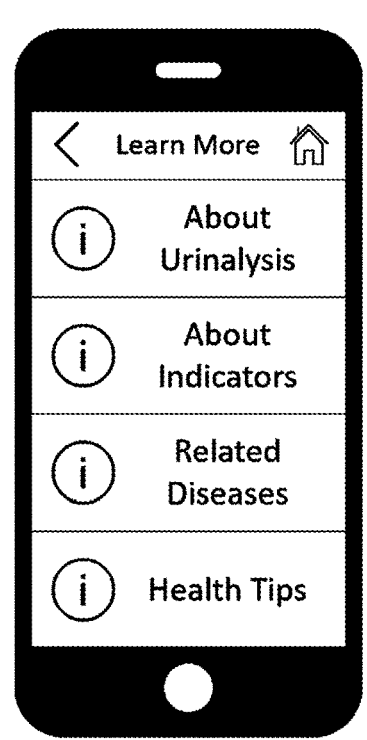
FIG. 21 is an illustration of a mobile app information display.

The health guide page, shown in FIG. 21, provides essential information for the user to learn more about urinalysis, different indicators, urine-related diseases, and useful health tips.

Thus it has been shown and described a method and system for collecting and analyzing urine samples. Since certain changes may be made in the present disclosure without departing from the scope of the present invention, it is intended that all matter described in the foregoing specification and shown in the accompanying drawings be interpreted as illustrative and not in a limiting sense.

The invention claimed is:

1. A urine collecting and analyzing apparatus adapted to mount on a toilet having a bowl with a rim, and front, and two sides, the apparatus comprising:
   (a) a housing adapted to mount on the rim of the bowl and having an opening in the center adapted to make the bowl accessible;
   (b) a collector cup having a collecting position over the bowl and a retracted position under a floor of a collector compartment in the housing at one side of the bowl, the collector cup, when in the collecting position, adapted to capture urine released by a user;
   (c) a mechanism in the housing for moving the collector cup between the collecting position and the retracted position;
   (d) a measurement chamber extending downwardly from the housing into the bowl at other side of the bowl;
   (e) a transfer tube fluidly connecting the collector cup to the measurement chamber such that urine flows from the collector cup into the measurement chamber to at least a predetermined threshold volume and level;
   (f) sensors for measuring parameters of urine extending into the measurement chamber below the threshold level; and
   (g) a controller for reading the sensors and transmitting sensor data to a device for storage and display.

2. The urine collecting and analyzing apparatus of claim 1 further comprising a flushing mechanism comprising:
   (a) a flush valve controlled by the controller and having an inlet and an outlet, the inlet fed from a water supply;
   (b) a flush tube from the flush valve outlet to an opening in the collector compartment floor above the collector cup when in the retracted position;
   (c) a drain in the bottom of the measurement chamber; and
   (d) a drain plug controlled by the controller to open and close the drain.

3. The urine collecting and analyzing apparatus of claim 2 wherein the flush mechanism further comprises a sealing gasket between the collector compartment floor and the urine collector cup.

4. The urine collecting and analyzing apparatus of claim 1 wherein the mechanism for moving the urine collector cup is operated manually.

5. The urine collecting and analyzing apparatus of claim 1 wherein the mechanism for moving the urine collector cup comprises:
   (a) an arm extending from the cup into and along the housing;
   (b) an elongated curved slot in the arm;
   (c) a pin in the housing extending through the slot;
   (d) a tab attached to the arm and accessible through a slit in the housing;
   (e) whereby, the cup is moved from the retracted position to the collecting position by pushing the tab along the slit.

6. The urine collecting and analyzing apparatus of claim 1 wherein the mechanism for moving the urine collector cup is motorized.

7. The urine collecting and analyzing apparatus of claim 1 wherein the mechanism for moving the urine collector cup is operated automatically.

8. The urine collecting and analyzing apparatus of claim 1 wherein the apparatus includes a means for determining the urine level in the measurement chamber.

9. The urine collecting and analyzing apparatus of claim 1 wherein the transfer tube includes a flow-rate sensor to permit the controller to determine the amount of liquid flowing into the measurement chamber.

10. The urine collecting and analyzing apparatus of claim 1 wherein the measurement chamber further comprises an overflow outlet to prevent an excess of urine in the measurement chamber.

11. The urine collecting and analyzing apparatus of claim 1 wherein urine flows from the collector cup into the measurement chamber via gravity.

12. The urine collecting and analyzing apparatus of claim 1 wherein the device is a mobile device with an app for personalized configuration, control, monitoring, and data storage.

* * * * *